(12) United States Patent
Klunder et al.

(10) Patent No.: US 9,114,395 B2
(45) Date of Patent: Aug. 25, 2015

(54) CARTRIDGE FOR AN AMPLIFICATION PROCESS

(75) Inventors: Derk Jan Wilfred Klunder, Eindhoven (NL); Anke Pierik, Eindhoven (NL); Richard Joseph Marinus Schroeders, Eindhoven (NL); Marius Iosif Boamfa, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 13/264,187

(22) PCT Filed: Apr. 13, 2010

(86) PCT No.: PCT/IB2010/051584
§ 371 (c)(1),
(2), (4) Date: Oct. 13, 2011

(87) PCT Pub. No.: WO2010/119396
PCT Pub. Date: Oct. 21, 2010

(65) Prior Publication Data
US 2012/0035075 A1    Feb. 9, 2012

(30) Foreign Application Priority Data
Apr. 15, 2009  (EP) .................................. 09157918

(51) Int. Cl.
*B01L 3/00*    (2006.01)
*B23P 11/00*   (2006.01)
*B01L 7/00*    (2006.01)
*C40B 60/12*   (2006.01)
(Continued)

(52) U.S. Cl.
CPC ............. *B01L 3/5027* (2013.01); *B01L 7/52* (2013.01); *B01J 2219/00608* (2013.01); *B01L 9/52* (2013.01); *B01L 9/527* (2013.01); *B01L 2200/025* (2013.01); *B01L 2200/141* (2013.01); *B01L 2300/0609* (2013.01); *B01L 2300/0636* (2013.01); *B01L 2300/0816* (2013.01); *B01L 2300/0819* (2013.01); *B01L 2300/0858* (2013.01); *B01L 2300/0887* (2013.01); *G01N 2035/00158* (2013.01); *Y10T 29/49826* (2015.01)

(58) Field of Classification Search
CPC .................................................. B29C 66/43421
USPC ....................................... 422/552, 554; 506/9
See application file for complete search history.

(56) References Cited

U.S. PATENT DOCUMENTS 7,001,572 B1 * 2/2006 Gueritault et al. ............ 422/68.1
7,294,478 B1 * 11/2007 Hinchcliffe .................... 435/7.9
(Continued)

FOREIGN PATENT DOCUMENTS

| EP | 1762300 A2 | 3/2007 |
| WO | 0141931 A1 | 6/2001 |
| WO | 2009111696 A1 | 11/2009 |

*Primary Examiner* — Jennifer Wecker

(57) ABSTRACT

The invention relates to real-time array PCR cartridges. The cartridge (100) has a fluid chamber (101) for a fluid bath (102) and a first support element (200) for fixing a microarray (103) in the fluid chamber (101). Thereby the first support element (200) fixes the microarray (103) in such a way that a change of a size of the microarray (103) due to thermal expansion of the microarray (103) is possible without inducing substantial mechanical stress to the cartridge (100). Thereby the cartridge materials chosen independently from thermal expansion coefficients of different microarrays that are to be inserted and fixed into the cartridge (100).

14 Claims, 5 Drawing Sheets

(51) Int. Cl.
*G01N 35/00* (2006.01)
*B01L 9/00* (2006.01)

(56) References Cited

U.S. PATENT DOCUMENTS

2002/0192701 A1* 12/2002 Adey ............................... 435/6
2003/0113724 A1* 6/2003 Schembri et al. .................. 435/6
2004/0005720 A1* 1/2004 Cremer et al. ................. 436/518
2004/0208792 A1* 10/2004 Linton et al. ..................... 422/99
2007/0009958 A1* 1/2007 Nagino et al. .................. 435/7.1
2007/0077580 A1* 4/2007 Ikeda et al. ....................... 435/6
2007/0098600 A1 5/2007 Kayyem
2007/0177457 A1* 8/2007 Hafner .......................... 366/208
2008/0207461 A1* 8/2008 Ermantraut et al. .............. 506/8

* cited by examiner

CARTRIDGE FOR AN AMPLIFICATION PROCESS

FIELD OF THE INVENTION

The invention relates to molecular diagnostics. In particular, the invention relates to a cartridge for an amplification process, a method for fixing a microarray in a cartridge in which an amplification process is carried out, a thermocycler for processing an amplification process, and a thermocycler that contains a microarray for monitoring an amplification process or detecting products of the amplification process on the microarray.

BACKGROUND OF THE INVENTION

Molecular biology research methods evolve through the development of the technologies used for carrying these methods out. Due to technical difficulties it may not be possible to analyze a large number of genes using traditional methods. Deoxyribonucleic acid (DNA) microarray is one such technology which enables the researchers to investigate and address issues which were once thought to be non-traceable. One may analyze the expression of many genes in a single reaction quickly and in an efficient manner. DNA microarray technology has empowered the scientific community to understand the fundamental aspects underlining the growth and development of life as well as to explore the genetic causes of anomalies occurring in the functioning of the human body.

A typical microarray experiment involves the hybridization of an mRNA molecule to the DNA template from which it is originated. Many DNA samples are used to construct an array. The amount of mRNA bound on the array indicates the expression level of the various genes. This number may run in thousands. All the data may be collected and a profile may be generated for gene expression in the cell.

In addition to that the polymerase chain reaction (PCR) is a technique widely used in molecular biology. A DNA polymerase is used to amplify a piece of DNA by an in vitro enzymatic replication. As PCR progresses, the DNA generated is used as a template for replication. This sets in motion a chain reaction in which the DNA template is exponentially amplified. Furthermore, real-time PCR (rtPCR) or quantitative PCR is used to measure the quantity of a PCR product preferably in real-time. rtPCR is the method of choice to quantitatively measure starting amounts of for example DNA. Real-time PCR is commonly used to determine whether for example a DNA sequence is present in a sample and the number of its copies in the sample. Real-time PCR methods use fluorescent dies or fluorophore containing DNA probes to measure the amount of amplified product in real-time.

An alternative to real-time PCR, with a potentially higher multiplexing grade, is real-time array PCR where the amplicons during at least one of the PCR cycles are hybridized on an array containing regions where amplicons can specifically hybridize to capture probes with a sequence matching part of the sequence of the amplicons.

An essential requirement for real-time array PCR is a cartridge that can withstand the thermally induced stress during the temperature cycling, in which different varying temperature fields are generated by a thermocycler, processing a desired PCR protocol.

SUMMARY OF THE INVENTION

It may be an object of the invention to provide for simplified amplification process measurements.

The described embodiments similarly pertain to a cartridge for processing an amplification process, a method for fixing a microarray in a cartridge for processing an amplification process, an instrument for processing an amplification process and the use of a cartridge for an amplification process. Synergetic effects may arise from different combinations of the embodiments although they might not be described herein in detail.

Further on, it shall be noted that all embodiments of the present invention concerning a method, may be carried out with the order of the steps as described, nevertheless this has not to be the only and essential order of the steps of the method. All different orders and combinations of the method steps are herewith disclosed.

In the context of the present invention the term "amplification process" comprises PCR as well as other procedures like e.g. nucleic acid sequence based amplification for RNA or DNA (NASBA), transcription mediated amplification for RNA (TMA) and rolling circle amplification for DNA (RCA). Also other molecular diagnostic amplification methods may be comprised.

In the context of the present invention the term "microarray" shall be used similarly to the term "array". The term microarray may also refer to a substrate with one or more microarrays on it (for example one microarray on the upper side and one on the lower side of the substrate).

Furthermore the term "thermal expansion" shall comprise in the context of the present invention an increase and a decrease of the size of the microarray due to temperature differences. The temperature differences may further be caused during a non-isothermal amplification process like e.g. PCR or before or after an isothermal amplification process like e.g. NASBA.

The term "support element" shall in the context of the invention be understood as any element, item or device being able to fix a microarray inside the cartridge, wherein the fixation is further defined hereinafter. Thereby the microarray may e.g. be embodied as a microscope slide. The support element may be physically separated from the cartridge but may also be a physical part of the cartridge. Examples for a support element may be any protrusions from the inner wall of the fluid chamber. Such a protrusion may have e.g. a beam shape and may be manufactured out of one piece together with the spacer material of the cartridge. If desired a plurality of support elements may be provided by the cartridge. The support element may be flat to allow good contact between the surface of the support element and a microscope slide being used as the microarray. Also a foil may be an embodiment of a support element.

According to an exemplary embodiment of the invention a cartridge for processing an amplification process is presented, wherein the cartridge comprises a fluid chamber for a fluid bath and a first support element for fixing a microarray in the fluid chamber. Thereby the first support element is adapted for fixing the microarray in the fluid chamber in such a way, that a change of a size of the microarray due to thermal expansion of the microarray is possible without inducing substantial mechanical stress to the cartridge, even if a first thermal expansion coefficient of the microarray differs from a second thermal expansion coefficient of the cartridge.

It shall explicitly be noted that the amplification process may be the non isothermal process of PCR. In other words according to another exemplary embodiment of the invention a cartridge for processing PCR is presented, wherein the cartridge comprises a fluid chamber for a fluid bath and a first support element for fixing a microarray in the fluid chamber. Thereby the first support element is adapted for fixing the microarray in the fluid chamber in such a way, that a change of a size of the microarray due to thermal expansion of the microarray is possible without inducing substantial mechanical stress to the cartridge, even if a first thermal expansion coefficient of the microarray differs from a second thermal expansion coefficient of the cartridge.

In other words, during thermocycling of an amplification process like e.g. a PCR process the expansion of the microarray due to the temperature difference caused during the different cycles of the PCR do not have any destroying effect on the cartridge. The microarray may for example expand during different PCR cycles without any counter pressure, without any bending or any deflection of the microarray. The avoidance of such a bending due to the fixation according to the invention may lead to improved and more exact optical detection possibilities of hybridized DNA on the microarray. That may be the case because spatial requirements for the position of the microarray during an optical detection originating from e.g. the focal field of the detection unit can be met by the fixation of the array according to the invention. In other words the microarray is fixed in such a way inside the cartridge that it is neither bending out of the focal field during PCR nor is it inducing substantial mechanical stress that may create a malfunction or breakage of the cartridge.

Another important aspect of this exemplary embodiment of the invention is, that the before mentioned advantages of this embodiment are independent from the material choice of the microarray and the material choice of the cartridge elements like the fluid chamber. This may make it possible to easily integrate different arrays made out of different substrate materials without having the need to match the mechanical properties of the array with the other materials of the cartridge. For example, the thermal expansion coefficient of the array and the thermal expansion coefficient of any element of the cartridge must not be matched for doing a real-time array PCR process or measurement.

This means that the materials of the different elements constituting the cartridge like e.g. a base plate, a lid and spacer material can be optimized with respect to their thermal expansion coefficients (e.g. matching of these thermal expansion coefficients) in order to avoid mechanical stress and/or leakage due to a cartridge break for the cartridge used for PCR without having the need to take the microarray and its material and/or geometry into account. This may lead to a universal useable cartridge which may reduce production cost for a cartridge manufacturer, as the bandwidth of the needed cartridges may be reduced. It shall explicitly be noted that a group constituting the cartridge may comprise additional elements to the base plate, the lid and the spacer material.

This exemplary embodiment of the invention may provide for a leakage free cartridge that is independent of the material of the desired and used array. This again leads to a true modular application of the cartridge as one and the same cartridge may be used for different array substrates comprising different array materials and/or geometries.

As the microarray is fixed with the first support element inside of the fluid chamber a more tolerant handling of the cartridge is reached. As the microarray is inside of the cartridge a lower risk of contamination of the array is realized.

Furthermore the ability to match the cartridge materials without simultaneously determining the materials that can be used for a microarray in combination with the cartridge reduces deformation or fracture risk of the cartridge itself due to different thermal expansion coefficients of for example the lid and the base plate. A leakage of the fluid in the fluid chamber may thus be avoided. This may reduce contamination risks of the surrounding of the cartridge.

In other words, this exemplary embodiment of the invention is suitable for a large range of different materials of microarrays without having to modify the materials of the constituting elements of the cartridge.

An alternative to real-time PCR, with a potentially higher multiplexing grade, is real-time array PCR where the amplicons during at least one of the PCR cycles are hybridized on an array containing regions where amplicons can specifically hybridize to capture probes with a sequence matching part of the sequence of the amplicons.

In case of a non isothermal time period before or after the actual amplification process, which itself may be isothermal, a thermal expansion of the microarray is also possible without any counter pressure. This may be the case for an amplification method which is isothermal but which starts at a constant temperature diverting from room temperature. Also any bending or any deflection of the microarray may thus be avoided. Therefore no substantial mechanical stress induction is created before or after the isothermal amplification process which stress may create a malfunction or disadvantageous breakage of the cartridge.

According to another exemplary embodiment of the invention, the first support element is adapted for positioning the microarray in a geometric plane in the fluid chamber and wherein the first support element is adapted for fixing the microarray in such a way that a two-dimensional movement of the microarray in the geometric plane due to the thermal expansion of the microarray is possible.

Thereby the geometric plane may be seen as the in-plane of the microarray.

It shall explicitly be noted, that the term geometric plane may also comprise that the microarray has a finite thickness, but the surface of the microarray may be predominantly determined by the two parallel surfaces building an underlayment for samples to be immobilized on the microarray.

In other words, the fixation of the microarray by the first support element is performed in such a way that at least two degrees of freedom for expanding movements of the microarray during thermal expansion is possible. It shall explicitly be noted that also a three-dimensional movement of the microarray is possible.

For example, a clamping of the microarray at only one lateral end of the microarray may provide for such a thermal expansion possibility of the microarray during PCR cycles.

According to another exemplary embodiment of the invention the first support element is adapted for fixing the microarray in the fluid chamber in such a way, that the microarray is entirely surrounded by a fluid bath.

It shall explicitly be noted that this technical feature of the fixation of the microarray enabling a complete flushing of the two main surfaces of the microarray in the same fluid bath can be independently realized by this exemplary embodiment of the invention from the fixation of the microarray by the first support element enabling a change of size of the microarray due to thermal expansion of the microarray without inducing substantial mechanical stress to the cartridge even if a first thermal expansion coefficient of the microarray differs from the second thermal expansion coefficient of the cartridge.

In other words, the advantages of fixing the array in the fluid chamber in such a way that both main surfaces of the microarray on which samples may be immobilized are contacted with the same fluid bath a heat exchange in the fluid bath is always possible avoiding bending of the microarray due to temperature differences at e.g. the two main surfaces. In addition to that a higher throughput may be realized with that exemplary embodiment of the invention, as both sides may be used for e.g. PCR.

In other words, the microarray, which may have two main surfaces for providing an underlayment for samples, is surrounded by only one fluid bath. Thereby the term fluid bath shall be understood in such a way, that different areas of the fluid bath are directly connected by the fluid of the fluid bath in such a way that if temperature differences between these areas occur that a thermal exchange between these areas is possible by e.g. heat exchange via the fluid.

This arrangement of the microarray in the fluid bath in the fluid chamber has at least the following two advantages. A thermal bending of the microarray due to different temperatures in different areas may be avoided as these differences are equalized by means of for example heat exchange within the fluid.

In addition to that a second advantage is realized by the fact that both sides/main surfaces of the microarray can be used for measuring hybridization of PCR products to the capture probes on the microarray. In other words, both main surfaces of the microarray can be used for PCR. As samples on both sides are provided with the same fluid surrounding equal chemical reaction conditions are provided for every sample.

In order to be able to detect on both sides of the microarray sample characteristics e.g. a scanning confocal optical unit may be used where a user may switch from the upper main surface to the lower main surface of the microarray.

According to another exemplary embodiment of the invention, a microarray for an amplification process is comprised within the cartridge. Furthermore the microarray has an upper main surface and a lower main surface and wherein the first support element fixes the microarray in such a way, that the upper and lower main surfaces are surrounded by the fluid bath.

It shall explicitly be noted that the microarray may be embodied as an array for array PCR.

According to another exemplary embodiment of the invention, the first support element extends at least partially from an inner wall of the cartridge into the liquid chamber.

The first support element may for example be arranged at a spacer material wherein the spacer material builds a connection between the lid and the base plate of the cartridge. Furthermore the first support element may for example be arranged in position which cuts the distance from the lid to the base plate in half.

According to another exemplary embodiment of the invention, the first support element has a beam shape.

According to another exemplary embodiment of the invention, the cartridge comprises a second support element for an additional fixing of the microarray, wherein the second support element is adapted for additionally fixing the microarray in such a way, that it allows for a sliding movement of the microarray over the second support element during the change of the size of the microarray due to thermal expansion of the microarray.

In other words, the microarray is firstly fixed by the first support element and is secondly and additionally fixed by the second support element. Thereby the first fixing enables at least a two-dimensional thermal expansion movement of the array as described above and the additional fixing by the second support element additionally supports and fixes the microarray in the fluid chamber but simultaneously allows a change in size of the microarray. The second support element in combination with the first support element fixes the microarray in such way that during such a thermal expansion movement the array slides over the second support element.

According to another exemplary embodiment of the invention, the second support element is arranged in the fluid chamber in such a way, that it provides for an underlayment for the microarray when the microarray is fixed by the first support element.

In other words, the second support element holds the microarray in a horizontal direction and avoids deflection of the microarray perpendicular to this horizontal direction wherein the horizontal direction is parallel to the in-plane formed by the microarray and thus parallel to main surfaces of the microarray. Simultaneously, the second support element provides for the possibility of the microarray to slide over the second support element when it changes its size due to thermal expansion during a PCR cycle.

It shall explicitly be noted that also a third, a fourth, a fifth and more support elements may be arranged to fix and/or support the microarray. The array may be mounted on top of the support elements that may be shaped e.g. as beams to fix the vertical position of the array.

According to another exemplary embodiment of the invention, the cartridge further comprises a base plate, a lid and spacer material being arranged between the base plate and the lid wherein the base plate, the lid and the spacer material are together arranged in such a way that the liquid chamber is formed.

According to another exemplary embodiment of the invention, at least one of the lid and the base plate has at least one of a fluid inlet and a fluid outlet.

In order to flush the fluid chamber with the desired fluid for providing for example primers, dyes, and chemical reaction surroundings for processing complete PCR protocols a fluid inlet and outlet is provided by the cartridge. The inlet and outlet may for example be arranged at the lid or may for example be arranged at the base plate. Also other combinations are possible.

According to another exemplary embodiment of the invention, the first support element comprises a clamp wherein the microarray is fixed by the clamp.

In other words, the in-plane, horizontal position of the microarray is fixed by a single clamp. Because the microarray is fixed by only a single clamp, it can still expand in the in-plane direction by sliding along for example the second support element. A simultaneous optical measurement of the samples being immobilized on the two main surfaces of the array is not disturbed by such a two-dimensional expansion movement of the array as the focal field of such an optical detection unit is not left by the array as bending of the array due to temperature differences on both sides of the main surfaces is avoided due to an open fluid bath.

According to another exemplary embodiment of the invention, the spacer material and the base plate are connected together by laser welding, molding, and/or melting and wherein the spacer material and the lid are connected together by laser welding.

In this exemplary embodiment of the invention the presence of glue in the cartridge can be avoided and thus the risk of inhibition of the PCR reaction by the glue can be avoided. For example, the cartridge materials like the materials of the spacer material, the base plate and the lid are thermoplastic materials such as polypropylene. The fluidics and the fluid chamber may be defined by injection molding of the spacer. The polypropylene spacer may be blackened to facilitate the required absorption of the laser power during the laser welding. The lid and the base plate may for example be made of flexible polypropylene foil that may be connected to the spacer material by laser welding. Before welding of the foils, the microarray may be mounted into the cartridge.

According to another exemplary embodiment of the invention, the cartridge comprises a heater wherein the heater is adapted to cause thermocycling in the fluid bath.

In order to process complete PCR protocols, different temperature evolutions in the fluid chamber have to be initiated. These requirements may be met by the heater comprised by the cartridge. Thereby different positions of the heater may be possible as long as PCR cycles may be initiated by the heater. The heater may also be separate from the cartridge. The system (thermocycler) may contain the heater.

According to another exemplary embodiment of the invention an instrument for processing an amplification process and for containing a cartridge is presented. The instrument comprises thermocycler for processing an amplification process. The instrument further comprises a cartridge according to one of the above-mentioned exemplary embodiments and wherein the instrument further comprises an optical detection unit to optically analyze areas at which capture probes are immobilized at a microarray. Furthermore the instrument comprises a heater wherein the heater is adapted to cause thermal cycling in a fluid bath within the cartridge.

It shall explicitly be noted that the amplification process may be PCR. In other words according to another exemplary embodiment of the invention an instrument for processing PCR and for containing a cartridge is presented. The instrument comprises thermocycler for processing an amplification process. The instrument further comprises a cartridge according to one of the above-mentioned exemplary embodiments and wherein the instrument further comprises an optical detection unit to optically analyze areas at which capture probes are immobilized at a microarray. Furthermore the instrument comprises a heater wherein the heater is adapted to cause thermal cycling in a fluid bath within the cartridge.

In contrast to known technologies the microarray may be surrounded by the fluid in the fluid bath on both sides. For real-time array PCR the fluid may comprise a high concentration of fluorescently labeled primers or nucleotides. Therefore, a volume specific detection method may be required to suppress the background wherein the detection volume is limited to a small region.

According to another exemplary embodiment of the invention a use of the above and in the following described cartridge for an amplification process is presented.

It shall explicitly be noted that according to another exemplary embodiment of the invention the use of the above and in the following described cartridge for real time array PCR is presented.

According to another exemplary embodiment of the invention, a method for fixing a microarray in a cartridge for processing an amplification process is presented wherein the method comprises the following steps: Providing for fluid chamber in the cartridge for a fluid bath, providing for a first support element, fixing the microarray and the fluid chamber with the first support element, wherein the fixing of the microarray and the fluid chamber is adapted in such a way that a change of a size of the microarray due to a thermal expansion is possible without inducing substantial mechanical stress to the cartridge if the first thermal expansion coefficient of the microarray differs from a second thermal expansion coefficient of the cartridge.

It shall explicitly be noted that the method may relate to PCR. In other words according to another exemplary embodiment of the invention, a method for fixing a microarray in a cartridge for processing PCR is presented wherein the method comprises the following steps: Providing for fluid chamber in the cartridge for a fluid bath, providing for a first support element, fixing the microarray and the fluid chamber with the first support element, wherein the fixing of the microarray and the fluid chamber is adapted in such a way that a change of a size of the microarray due to a thermal expansion is possible without inducing substantial mechanical stress to the cartridge if the first thermal expansion coefficient of the microarray differs from a second thermal expansion coefficient of the cartridge.

In other words, the method allows to produce leakage free cartridges that may be comprised of material matched elements so that deformation due to thermal expansion during PCR cycles is avoided but simultaneously enable the use of different microarray materials. Furthermore the method has the advantage that the same cartridge may be used for different microarrays. Additionally a lower risk of contamination of the microarray is realized as it is fixed inside of the cartridge.

It may be seen as a gist of the invention that a cartridge for PCR is presented that is suitable for a large range of different microarrays, even for microarrays made of different materials without having to modify the materials of elements of the cartridge. In other words it may be seen as an gist of the invention to provide for simplified real-time array PCR measurements.

In addition to that another gist of the invention may be seen in a cartridge providing for the possibility to fix the array for PCR in such a way that both main surfaces of the microarray may be used for immobilizing samples in order to use both sides of the microarray for example hybridization and subsequent or simultaneous optical detection.

It has to be noted that the embodiments of the invention are described with reference to different subject-matters. In particular, some embodiments are described with reference to apparatus type claims whereas other embodiments are described with reference to method type claims. However, a person skilled in the art will gather from the above and the following description that unless other notified in addition to any combination or features belonging to one type of subject-matter also any combination between features relating to different subject-matters is considered to be disclosed within this application.

The aspects defined above and further aspects, features and advantages of the present invention can also be derived from the examples of embodiments to be described hereinafter and are explained with reference to examples of embodiments. The invention will be described in more detail hereinafter with reference to examples of embodiments but to which the invention is not limited.

DETAILED DESCRIPTION OF THE DRAWINGS

Figure 1:
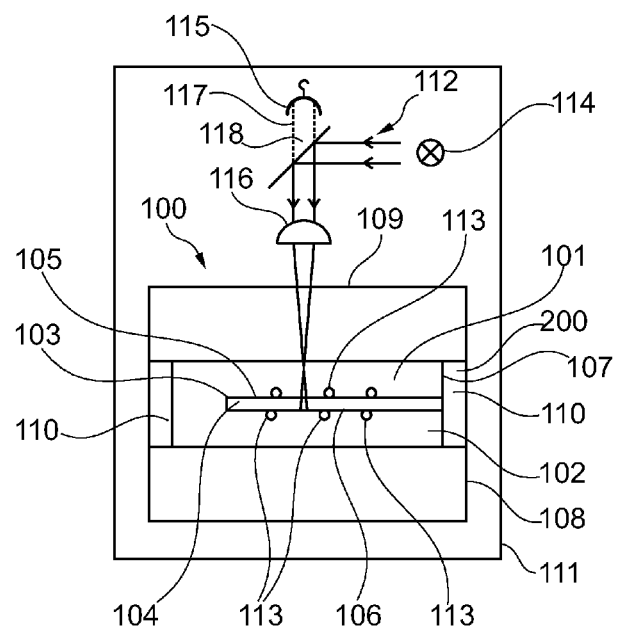
FIG. 1 schematically shows a thermocycler with a cartridge for PCR according to an exemplary embodiment of the present invention.

Similar or relating components in the figures are provided with the same reference numerals. The illustration in the figures are schematic and not fully scaled.

FIG. 1 shows a cartridge 100 for processing PCR wherein the cartridge comprises a fluid chamber 101 and a fluid bath 102. In other words the cartridge is adapted to withstand the thermal stress induced to the cartridge during a PCR process. Furthermore a microarray 103 is shown which contains areas/spots 113 where capture probes (typically ssDNA with a length around 20-60 nucleotides) are immobilized, the fluid 102 contains the target molecules that are amplicons generated during the PCR steps and that are to hybridize to the capture probes. Thereby the microarray is fixed in a geometric plane 104 which can be seen in FIG. 1 in a side view. Thereby the microarray has an upper main surface 105 and a lower main surface 106 which are used to position or immobilize the areas/spots 113 on the microarray as described above. In FIG. 1 the microarray is fixed at an inner wall 107 of the cartridge which cartridge may comprise a spacer material 110, a base plate 108 and a lid 109. In this exemplary embodiment of the invention the first support element 200 is formed by spacer material 110 shown on the right hand side of FIG. 1. As the microarray is clamped on only one side it can easily expand in the in-plane direction parallel to the plane of the lid.

Furthermore an instrument 119 comprising a thermocycler 111 for processing PCR cycles is shown in which the cartridge 100 is arranged. In addition to that an optical detection unit 112 is shown comprising at least an optical source 114 and an optical detector 115. Furthermore a lens 116 for focusing the light from the light source onto the microarray is comprised, as well as a dichroic mirror 118. The dichroic mirror reflects the light from the light source but transmits the fluorescence light 117 emitted from the microarray.

To detect on both sides of the microarray for example a scanning confocal setup may be used as the optical detection unit where one can switch from the upper to the lower plane of the microarray and vice versa.

Thereby the first support element may be formed by the spacer material 110 on the right-hand side on which the array 103 is horizontally fixed. Thereby the fixing of the microarray in the fluid chamber is arranged in such a way that a change of a size of the microarray due to thermal expansion of the microarray during for example PCR cycles is possible without inducing substantial mechanical stress to the cartridge even if a first thermal expansion coefficient of the microarray differs from a second thermal expansion coefficient of the cartridge.

Figure 4:
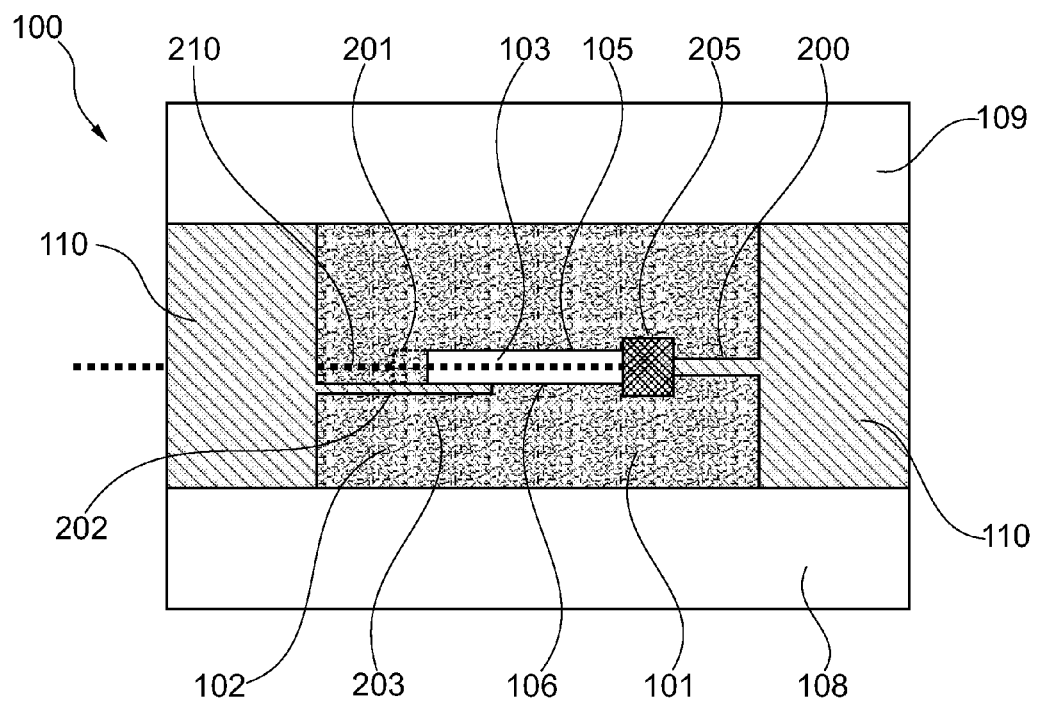
FIG. 4 schematically shows a cross-section of a cartridge according to another exemplary embodiment of the invention.

In other words, during PCR cycles the microarray 103 may for example expand to the left-hand side of the shown FIG. 4 and in the in/plane direction perpendicular to the plane of FIG. 1 without causing mechanical stress to the cartridge leading to substantial deformation or the disadvantages break of the cartridge.

When the surface of the microarray is scanned, a number of spots may be used that already give a signal. These spots may be used to put a grid over the array. In case the array expands over the horizontal plane, the spot locations may differ from the locations obtained during previous scans. But as gridding spots are available, the correct spot positions can be located.

It shall explicitly be noted that although this exemplary embodiment is described in relation to the amplification process of PCR it is also possible that this and other embodiments of the invention is for processing other amplification processes like e.g. nucleic acid sequence based amplification for RNA or DNA (NASBA), transcription mediated amplification for RNA (TMA) and rolling circle amplification for DNA (RCA). Although these processes may mainly be based on isothermal process steps, it may e.g. be required to initially reach a certain temperature deviating from room temperature. Thus also in these amplification methods thermal expansions of the array may occur.

Figure 2:
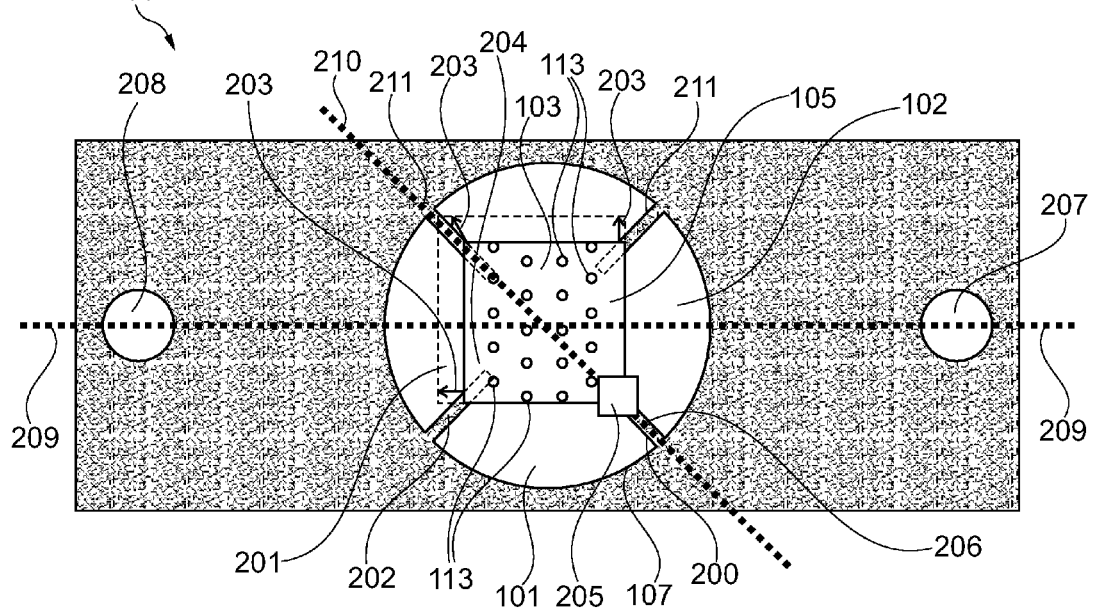
FIG. 2 schematically shows a cross-section of a cartridge according to an exemplary embodiment of the invention.

FIG. 2 further shows a cross-sectional view of the cartridge wherein the cross-section is parallel to the plane of the lid shown in FIG. 1. It can clearly be seen that the first support element 200 being for example shaped as a beam 206 has a clamp 205 in order to fix the microarray in the fluid chamber 101 containing the fluid bath 102 in such a way that a change of a size 201 of the microarray due to thermal expansion of the microarray is possible without inducing substantial mechanical stress to the cartridge, even if a first thermal expansion coefficient of the microarray differs from a second thermal expansion coefficient of the cartridge.

It can clearly be seen, that the microarray is clamped at only one side with the clamp 205 so that it may easily expand in the in-plane direction.

Furthermore a second support element 202 for an additional fixing of the microarray is shown in FIG. 2 wherein a sliding movement 203 of the microarray during the change of the size which is symbolically illustrated by the dotted lines of an enlarged microarray with reference numeral 201 which enlarged size may be present after an increase of temperature.

Furthermore the sliding movement of the microarray is symbolically illustrated by the arrows 203 wherein also additional third and fourth support elements 203 are shown. In other words, the shown support elements 202 and 203 are provided as underlayment for the microarray to fix the vertical position of the microarray. The horizontal position of the microarray is fixed by a single clamp 205. The clamp may have a spacing in which the microarray is clamped of at least the thickness of the array. The clamp may be made out of or may comprise a polymer like or polymer based material that may e.g. be deformed by laser welding. Thereby a high power laser may be focused on the interface such as polypropylene in order to make a connection between the clamp and the array. Additionally a fluid inlet 207 and a fluid outlet 208 are shown. Furthermore a first cross-section line 209 and a second cross-section line 210 are shown.

This top view shown in FIG. 2 by means of the symbolically illustrated change of size 201 and symbolically illustrated sliding movement 203 makes clear that this cartridge is suitable for a large range of different microarrays without having to modify the materials of the other elements of the cartridge like for example the base plate, the lid or the spacer material.

Figure 3:
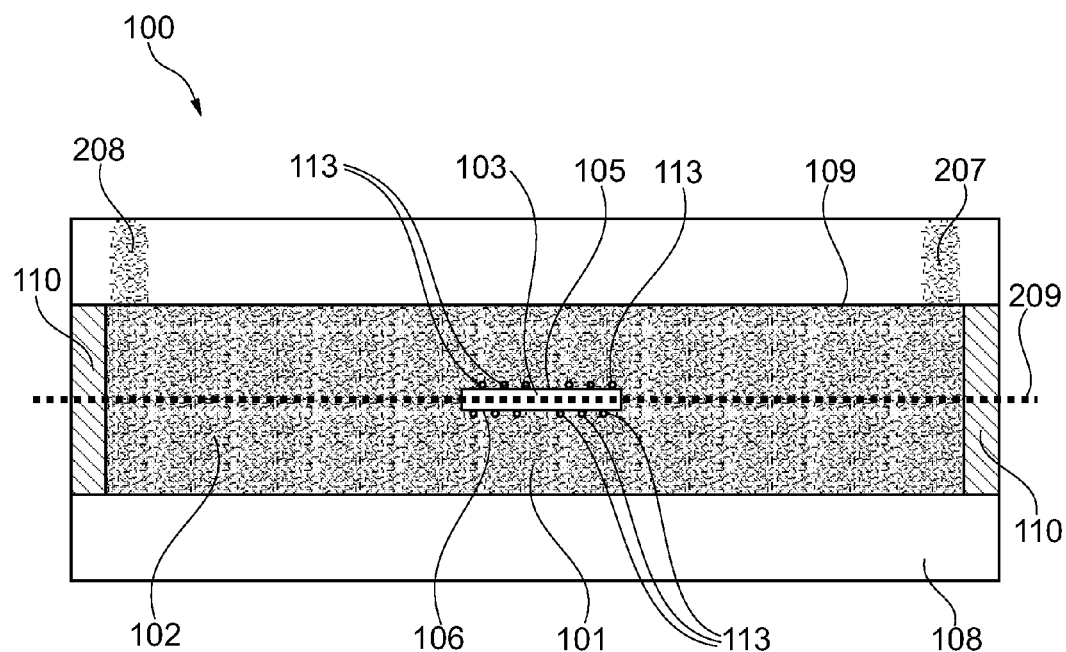
FIG. 3 schematically shows a cross-section of a cartridge according to another exemplary embodiment of the invention.

FIG. 3 shows a cross-section along the line 209 of FIG. 2. Thereby a cartridge 100 is shown with a fluid chamber 101 and a fluid bath 102. Thereby it can clearly be seen, that the first support element (not shown) fixes the array in such a way that the microarray is entirely surrounded by the fluid bath. Thus the upper main surface 105 and the lower main surface 106 may both be simultaneously provided with areas/spots 113 where capture probes are immobilized which increases the multiplexing capabilities of the example PCR process.

FIG. 3 shows according to another exemplary embodiment of the invention a cartridge 100 with a plate 108, a lid 109 and a spacer material 110 being arranged between the base plate and the lid wherein the base plate and the lid and the spacer material form the liquid chamber 101 for the fluid bath 102. It can clearly be seen that the first support element 200 is arranged nearly in the middle of the height of the spacer material 110 and the first support element further elongates horizontally into the fluid chamber 101. The first support element further comprises a clamp 205 which fixes the microarray and the fluid chamber in such a way that the change of a size of the microarray due to thermal expansion of the microarray is possible without inducing substantial mechanical stress to the cartridge. This advantage is also present if the thermal expansion coefficients between the cartridge and the microarray differ. In addition to that FIG. 4 shows the change of the size by the dotted line 201 describing a situation in which the microarray 103 has been expanded. During this thermal expansion the array is horizontally fixed by the first support element 200 and is vertically fixed by the second support element 202. Simultaneously, the additional fixation by the second support element 202 is arranged in such a way that a sliding movement symbolically illustrated by the arrow 203 is possible for the microarray.

Therefore, different exchangeable arrays may be used within the same cartridge wherein during PCR cycles an optical detection by for example a confocal optical setup analyzing the upper main surface 105 and the lower surface 106 is not disturbed during expansions caused by PCR cycles having different temperature characteristics.

In other words, the constituting element of a cartridge 100 being for example the lid 109, the base plate 108 and the spacer material 110 may during material choice be matched with respect to their thermal expansion coefficients without automatically determining the material and/or geometry of the microarray to be fixed in the cartridge consequently having a predetermined thermal expansion coefficient. Therefore, any type of microarray material or substrate can easily be integrated in this embodiment of the invention.

Figure 5:
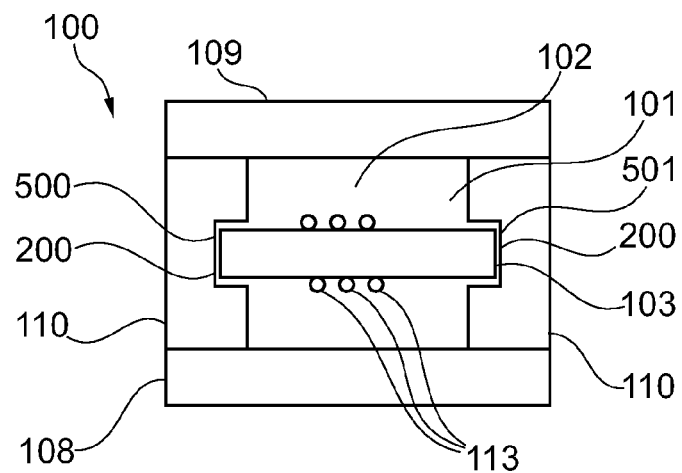
FIG. 5 schematically shows a cross-section of a cartridge according to another exemplary embodiment of the invention.

FIG. 5 shows another exemplary embodiment of the invention wherein in the cartridge 100 the array 103 is fixed by a first support element 200 which is formed by two U-shaped recesses 500 and 501 within the spacer material 110 wherein a fixation having the above-mentioned advantages is provided to the array.

Figure 6:
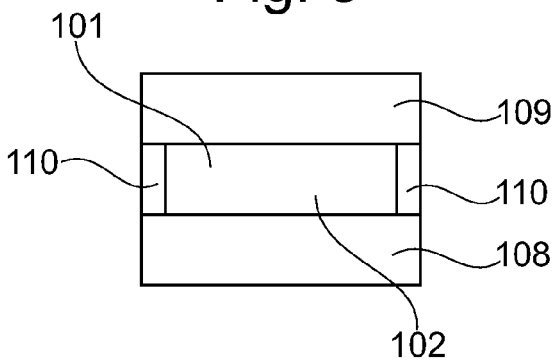
FIGS. 6, 7 and 8 schematically show deformation of a cartridge may be avoided by an exemplary embodiment of the invention.
Figure 7:
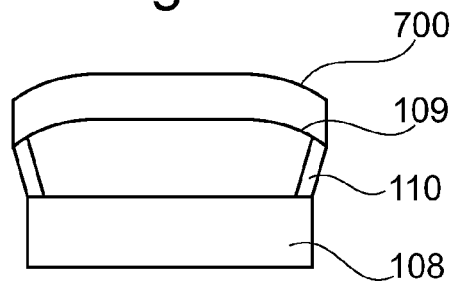
Figure 8:
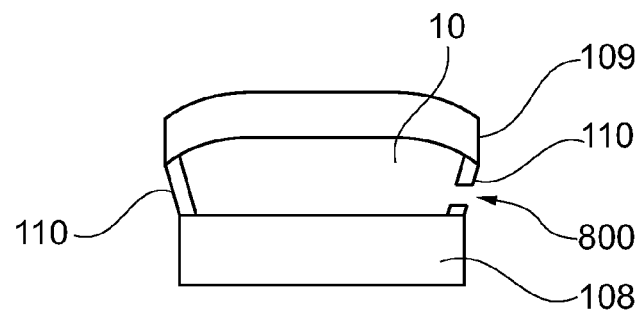

FIGS. 6, 7 and 8 show cartridges that may be deformed during PCR cycles, which effect may be avoided by the present invention.

Figure 9:
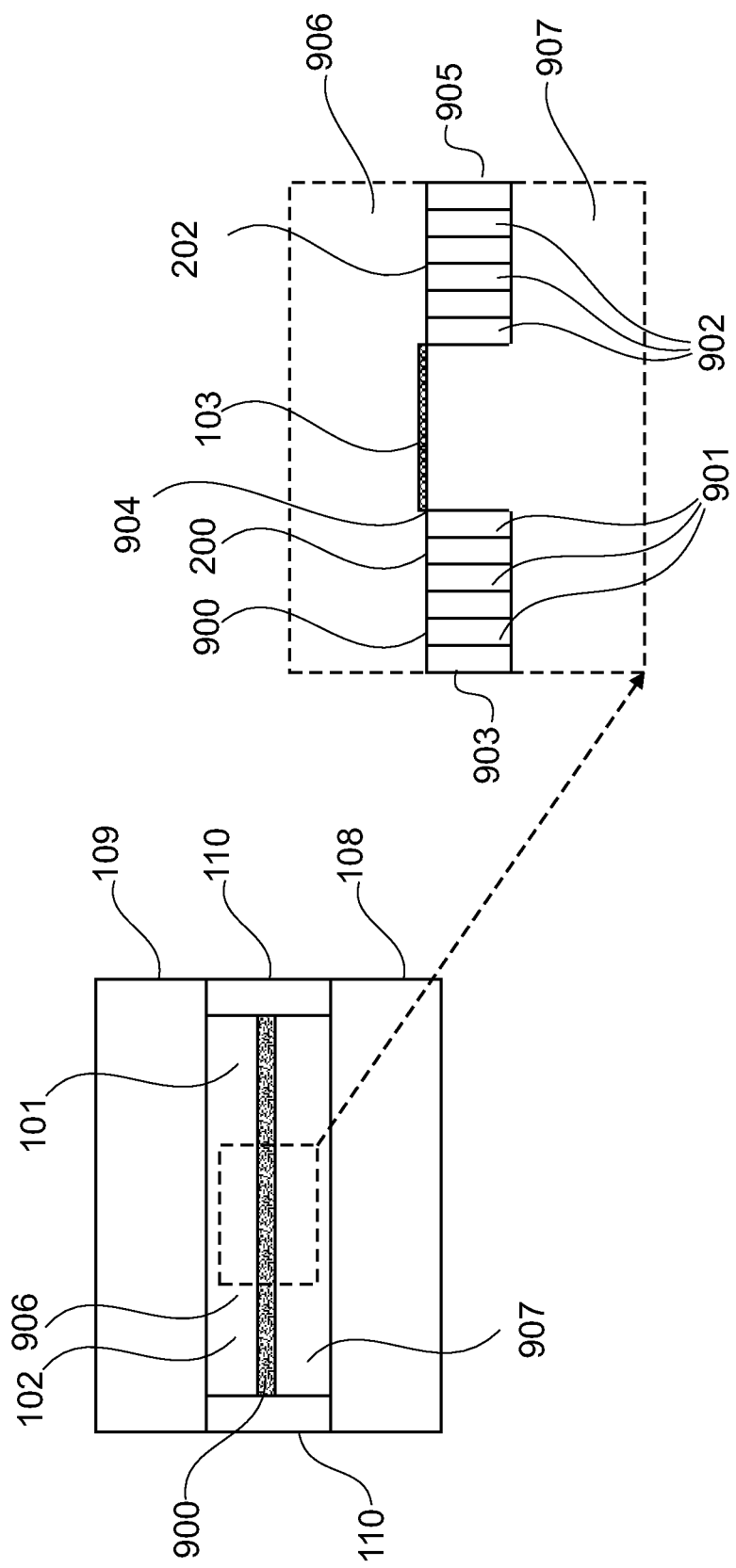
FIG. 9 schematically shows a cross-section of a cartridge according to another exemplary embodiment of the invention.

FIG. 9 shows an exemplary embodiment of the invention in which the microarray 103 may be fixed to another substrate 900 such as a foil that may be connected to the cartridge for example to the spacer material 110 on the left hand side of FIG. 9 in the lateral area 903. This may e.g. be done by laser welding. The substrate 900 as shown in the enlarged picture of the right-hand side of FIG. 9 may be perforated with apertures 901 that enable fluid to access both sides of the substrate.

The microarray 103 is fixed to the substrate 900 at the contact point 904. Different possibilities for fixing the array to the substrate are possible e.g. clamping and/or laser welding. Thus the substrate is an embodiment of the first support element 200 and is for fixing the microarray 103 in the fluid chamber. Thereby the first support element 200 is adapted for fixing the microarray in the fluid chamber in such a way that a change of a size of the microarray due to thermal expansion of the microarray is possible without inducing substantial mechanical stress to the cartridge, even if a first thermal expansion coefficient of the microarray differs from a second thermal expansion coefficient of the cartridge.

The second support element 202 also has perforations 902 and is contacted to the spacer material 110 in the lateral area 905. The microarray 103 is thus slideably supported by a further protrusion, which may also be a foil. It shall explicitly be noted that the first support element 200 and the second support element 202 divide the fluid chamber 102 into two sub chambers. The first sub chamber 906 being above the substrate 900 and the second sub chamber 907 being below the substrate 900. The perforations 901 might be useful to ensure fluidic contact between the two sub chambers so that a possibility to fix the array is provided in such a way that both main surfaces of the microarray may be used for immobilizing samples. Thus both sides of the microarray may be used for e.g. hybridization and subsequent or simultaneous optical detection. Also other amplification processes besides PCR may be used.

Therefore, the same temperature on both sides may be caused and thus a lower risk of thermal stress induced fracture may be realized. The foil may also be formed as a membrane. Instead of inserting the microarray into the cartridge it may also be possible that the array is fixed on slabs where in that case the slabs may be made out of the flexible foil.

Advantage of this embodiment may be a better fixation of the array to the cartridge.

Figure 10:
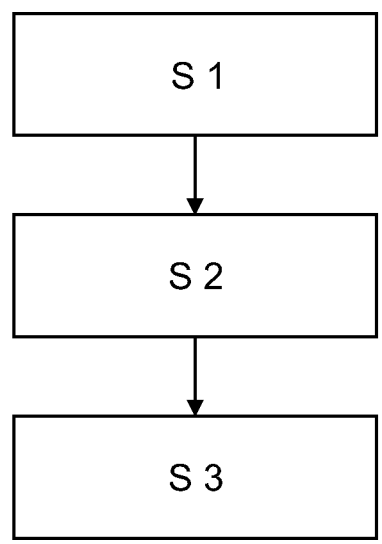
FIG. 10 schematically shows a flow diagram representing a method according to another exemplary embodiment of the invention.

FIG. 10 shows a flow diagram representing a method according to another exemplary embodiment of the invention. Thereby the method comprises the step S1 providing for a fluid chamber in the cartridge for a fluid bath and a step S2 providing for a first support element. Furthermore the step S3 is shown which step is fixing the microarray and the fluid chamber with the first support element, wherein the fixing of the microarray and the fluid chamber is adapted in such a way that a change of a size of the microarray due to thermal expansion is possible without inducing substantial mechanical stress to the cartridge, even if a first thermal expansion coefficient of the microarray differs from a second thermal expansion coefficient of the cartridge.

Other variations to the disclosed embodiment can be understood and effected by those skilled in the art in practicing the claimed invention, from the studying of the drawings, the disclosure and the appending claims. In the claims the word "comprising" does not exclude other elements or steps, and the indefinite articles "a" or "an" do not exclude a plurality. The mere effect that certain measures are recited in mutually different dependent claims does not indicate that a combination of these measurements cannot be used to advantage. Any reference signs in the claims should not be construed as limiting the scope of the claims.

The invention claimed is:

1. Cartridge for processing an amplification process, the cartridge comprising:
    a fluid chamber for a fluid bath; and
    a first support element comprising a clamp configured to position a microarray in a geometric plane in the fluid chamber and to clamp the microarray on only one corner so that a two-dimensional movement of the microarray in the geometric plane due to thermal expansion of the microarray is possible without inducing substantial mechanical stress to the microarray.

2. Cartridge according to claim 1,
    wherein the first support element is adapted for fixing the microarray in the fluid chamber in such a way, that the microarray is entirely surrounded by a fluid bath.

3. Cartridge according to claim 2, the cartridge further comprising:
   a microarray for an amplification process;
   wherein the microarray has an upper main surface and a lower main surface; and
   wherein the first support element fixes the microarray in such a way, that the upper and lower main surfaces are surrounded by the fluid bath.

4. Cartridge according to claim 1,
   wherein the first support element extends at least partially from an inner wall of the cartridge into the liquid chamber.

5. Cartridge according to claim 1,
   wherein the first support element comprises a beam so that the microarray may be mounted on top of the beam to fix the vertical position of the microarray.

6. Cartridge according to claim 1, the cartridge further comprising:
   a second support element for an additional fixing of the microarray;
   wherein the second support element is adapted for additionally fixing the microarray in such a way, that it allows for a sliding movement of the microarray over the second support element during the change of the size of the microarray due to thermal expansion of the microarray.

7. Cartridge according to claim 6,
   wherein the second support element is arranged in the fluid chamber in such a way, that it provides for an underlayment for the microarray, when the microarray is fixed by the first support element.

8. Cartridge according to claim 6, the cartridge further comprising:
   a base plate;
   a lid;
   a spacer material being arranged between the base plate and the lid;
   wherein the base plate, the lid and the spacer material are together arranged in such a way, that the fluid chamber is formed.

9. Cartridge according to claim 8,
   wherein at least one of the lid and the base plate has at least one of a fluid inlet and a fluid outlet.

10. Cartridge according to claim 8,
    wherein the spacer material and the base plate are connected together by at least one of laser welding, molding, and melting; and
    wherein the spacer material and the lid are connected together by laser welding.

11. An instrument for processing an amplification process and for containing a cartridge, the instrument comprising:
    a thermocycler for processing the amplification process;
    a cartridge according to claim 1;
    an optical detection unit to optically analyze areas at which capture probes are immobilized at a microarray; and
    a heater;
    wherein the heater is adapted to cause thermal cycling in a fluid bath within the cartridge.

12. Use of a cartridge according to claim 1 for an amplification process.

13. Method for fixing a microarray in a cartridge for an amplification process, the method comprising the steps:
    providing for a fluid chamber in the cartridge for a fluid bath;
    providing for a first support element comprising a clamp configured to position the microarray in a geometric plane in the fluid chamber; and
    clamping the microarray in the fluid chamber with the clamp on only one corner so that a two-dimensional movement of the microarray in the geometric plane due to thermal expansion of the microarray is possible without inducing substantial mechanical stress to the microarray.

14. Cartridge according to claim 1, wherein microarray is fixed only by a single clamp.

* * * * *